United States Patent [19]
Stevens et al.

[11] Patent Number: 5,545,527
[45] Date of Patent: Aug. 13, 1996

[54] METHOD FOR TESTING FOR MUTATIONS IN DNA FROM A PATIENT SAMPLE

[75] Inventors: John K. Stevens, Mississauga; James M. Dunn, Scarborough, both of Canada

[73] Assignee: Visible Genetics Inc., Toronto, Canada

[21] Appl. No.: 271,946

[22] Filed: Jul. 8, 1994

[51] Int. Cl.⁶ ............................. C12Q 1/68; C12Q 1/70; C12P 19/34; C07H 21/04
[52] U.S. Cl. ................. 435/6; 435/5; 435/91.2; 435/7.1; 435/7.9; 536/24.3; 536/24.32; 536/24.33; 530/388.1
[58] Field of Search .................................. 435/5, 6, 91.2, 435/7.1, 7.1–7.9; 536/24.3, 24.3–.33; 530/388.1

[56] References Cited

U.S. PATENT DOCUMENTS

| | | | |
|---|---|---|---|
| 4,016,043 | 4/1977 | Schuurs et al. | 195/103.5 R |
| 4,172,124 | 10/1979 | Koprowski | 424/85 |
| 4,474,893 | 10/1984 | Reading | 436/547 |
| 4,563,419 | 1/1986 | Ranki et al. | 435/6 |
| 4,582,788 | 4/1986 | Erlich | 435/6 |
| 4,683,194 | 7/1987 | Saiki et al. | 435/6 |
| 4,811,218 | 3/1989 | Hunkapiller et al. | 364/413.01 |
| 4,823,007 | 4/1989 | Hanson | 250/327.2 |
| 4,879,214 | 11/1989 | Kornher et al. | 435/6 |
| 4,971,903 | 11/1990 | Hyman | 435/6 |
| 5,062,942 | 11/1991 | Kambara et al. | 204/299 R |
| 5,091,652 | 2/1992 | Mathies et al. | 250/458.1 |
| 5,119,316 | 6/1992 | Dam et al. | 364/498 |
| 5,122,345 | 6/1992 | Tabor et al. | 422/116 |
| 5,137,806 | 8/1992 | LeMaistre et al. | 435/6 |
| 5,227,292 | 7/1993 | White et al. | 435/69.1 |
| 5,236,838 | 8/1993 | Rasmussen | 435/209 |
| 5,266,459 | 11/1993 | Beutler | 435/6 |

FOREIGN PATENT DOCUMENTS

| | | |
|---|---|---|
| 0390323 | 10/1990 | European Pat. Off. . |
| 390530 | 10/1990 | European Pat. Off. . |
| 89/06703 | 7/1989 | WIPO . |
| 92/00311 | 1/1992 | WIPO . |
| 94/00603 | 1/1994 | WIPO . |

OTHER PUBLICATIONS

Rychlik, W., "Selection of Primers for Polymerase Chain Reaction", *Methods in Molecular Biology*, vol. 15: *PCR Protocols: Current Methods and Applications*, pp. 31–40 (1993).

Dunn, et al., "Mutations in the RB1 Gene and Their Effects on Transcription",*Molecular and Cellular Biology* 9: 4596–4604 (1989).

Dunn, et al., "Identification of Germline and Somatic Mutations Affecting the Retinoblastoma Gene", *Science* 241: 1797–1800 (1988).

Orita, et al., "Detection of polymorphisms of human DNA by gel electrophoresis as single–strand conformation polymorphisms", *Proc. Nat'l. Acad. Sci. USA* 86:2766–2770 (1989).

(List continued on next page.)

Primary Examiner—Stephanie W. Zitomer
Assistant Examiner—Dianne Rees
Attorney, Agent, or Firm—Oppedahl & Larson

[57] ABSTRACT

A hierarchy of at least two assay techniques is utilized in testing for disease-associated mutations. The first assay in the hierarchy is selected to provide a highly specific test for the existence of the disease-associated mutation, although the accuracy of the test need not be high. The final assay in the hierarchy is selected to provide a highly accurate and highly specific test for the existence of the disease associated mutation. Intermediate tests of progressively greater accuracy may also be included in the hierarchy. Once the hierarchy has been selected for a given mutation-associated disease, a patient sample is analyzed the patient sample using the first, lowest accuracy assay in the hierarchy. If the result of the first assay is negative for the presence of a disease-associated mutation, then the next assay in the hierarchy is performed. This process is repeated until the final assay has been performed on all samples which gave negative results when tested by all less-accurate assays in the hierarchy. The test may be used for diagnosis and targeted screening for p53 mutations and mutations in the RB1 gene.

44 Claims, 4 Drawing Sheets

OTHER PUBLICATIONS

Savard–McQuigge et al., *Your Child has Retinoblastoma*, Canadian Cancer Society (1992), pp. 1–35.

Bull et al., "Rapid Misdiagnosis by *Mycobacterium avium–intracellulare* masquerading as tuberculosis in PCR/DNA probe tests", *The Lancet* 340: 1360 (1992).

Chamberlain, J. et al. "Detection of gene deletions using multiplex polymerase chain reactions." *Human Molecular Genetics*, Chapter 25, pp. 299–312, 1991.

Runnebaum, et al. "Mutations in p. 53 as potential molecular markers for human breast cancer" Proc. *Natl. Acad. Sci. USA*, vol. 88 12/91 pp. 10657–61, 1991.

Dunn et al., "Sequence based diagnosis of Retinoblastoma", Keystone Symposium on Tumor Suprresor Genes, Taos, New Mexico, Feb. 13–20, 1994, *J. Cellular Biochem Supp 18c:* p. 199 (1994).

McConkey, In Human Genetics: The Molecular Revolution, edited by Jones and Bontlett, 1993, pp. 192–197.

Lambkin et al., "Variations in Immunohistochemical Detection of p. 53 Protein Overexpression in Cervical Carcinomas with Different Antibodies and Methods of Detection", *J. Pathology* 172:13–18 (1994).

Baas, et al. "An Evaluation of Six Antiboides for Immunohistochemistry of Mutant p. 53 Gene Product in Archival Colorectal Neoplasms", *J. Pathology* 172: 5–12 (1994).

Hall et al., "p. 53 in Tumor Pathology: Can We Trust Immunohistochemistry—Revisited?", *J. Pathology* 172:1–4 (1994).

Beebe et al., "Incidence of *Neisseria gonorrhoeae* Isolates Negative by Syva Direct Fluoresecent–Antibody Test but Positive by Gen–Probe Accuprobe Test in a Sexually Transmitted Disease Clninc Population", *J. Clin. Microbiol.* 31: 2535–2537 (1993).

Bignon et al., "Expression of a retinpblastoma transgene in dwarf mice", *Genes & Devel.* 7: 1654–1662 ( 1993).

Breslauer et al., "Predicting DNA Duplex Stability from the Base Sequence", *Proc. Nat'l Acad. Sci.* 83: 3746–3750 (1986).

Eisenstein, B. I., "The Polymerase Chain Reaction", *N. Engl. J. Med.* 322: 178–183 (1990).

Erickson, D., "Diagnosis by DNA", *Scientific American* 267: 116 (1992).

Ewanowich, et al., "Major Outbreak of Pertussis in Northern Alberta, Canada: Analysis of Discrepant Direct Fluoresent–Antibody and Culture Results by Using Polymerase ChainReaction Methodology", *J. Clin. Microbiol.* 31: 1715–1725 (1993).

Hatcher et al., "Heteroduplex Formation: A Potential Source of Genotyping Error from PCR Products", *Prenatal Diagnosis* 13: 171–177 (1993).

Lee et al., "The retinoblastoma susceptibility gene encodes a nuclear phosphoprotein associated with DNA binding activity", *nature* 329: 642–645 (1987).

Roberts et al., "Direct Diagnosis of carriers of Duchene and Becker musclular dystrophy by amplification of lymphocyte RNA", *The Lancet* 336: 1523–1526 (1990).

Warren et al., "Comparative Evaluation of Detection Assays for *Chlamydia trachomatis*", *J. Clin. Microbiol.* 31: 1663–1666 (1993).

Kohler et al. Society for Gynecological Oncologists 23rd Annual Meeting, Mar. 15–18, p. 40.

Angelopoulou et al., The Cancer J. 6: 315–321.

Anderson et al. Anal. Chem 67: 377R–524R.

Landegran et al. Science 242: 229–237.

Goldberg and Diamandis, Clin Chem 39: 2360–2374.

| TEST | PERCENT POSITIVE | TEST/COST |
|---|---|---|
| PROTEIN IMMUNO | 20% | $12 |
| DNA PROBE | 40% | $50 |
| SEQUENCING LEVEL 1 | 25% | $100 |
| SEQUENCING LEVEL 2 | 15% | $600 |
| TOTAL TEST COST | | $182 |

```
                              EASY TO SEQUENCE
                              PREV. MUTATIONS           LEVEL 2A
                              EXONS 2-14, 17-19, 23

HARD TO SEQUENCE
                              PREV. MUTATIONS          LEVEL 2B
                              EXONS 1, 16, 20, 21, 22
SEQUENCE
ALL EXONS OF
RB1 GENE
                              EASY TO SEQUENCE
                              NO PREV. MUTATIONS       LEVEL 2C
                              EXONS 24, 25, 26, 27

HARD TO SEQUENCE
                              NO PREV. MUTATIONS       LEVEL 2D
                              EXON 15
```

FIG. 4

METHOD FOR TESTING FOR MUTATIONS IN DNA FROM A PATIENT SAMPLE

BACKGROUND OF THE INVENTION

This application relates to the testing of DNA from a patient sample for mutations, and more particularly to testing for mutations associated with cancer or other diseases for use in diagnosis and targeted screening.

It is becoming increasingly clear that many diseases are caused by genetic mutations. In some cases, these mutations are inherited. In others the mutations are acquired during the lifetime of the individual, for example as a result of exposure to radiation or carcinogenic chemicals. Early diagnosis and optimal treatment of diseases resulting from such mutations will often depend on the ability to detect the mutation, and in some cases to detect the specific nature of the mutation. To this end, various methods have been developed for testing for genetic mutations.

One class of tests makes use of immunodiagnostic techniques such as ELISA to detect the presence or absence of a protein product of the diagnostically important gene. Such tests make use of an antibody which selectively binds to either the normal protein product of the gene or the protein product of the mutated gene, and detect the presence or absence of binding. These tests are generally relatively low in cost. They suffer, however, from low clinical accuracy because they produce many false negative results. This has led workers in the field to question the value of immunodiagnostic tests for diagnosis of or screening for genetic diseases. See Beebe et al., *J. Clin. Microbiol.* 31: 2535–7 (1993); Warren, et al., *J. Clin. Microbiol.* 31:1663–6 (1993); Roberts et al., *The Lancet* 336:1523 (1990); De Cresce et al., *Medical Laboratory Observer* 25:28 (1993); Einstein et al., *New Engl. J. Med.* 322:178–183 (1990); Hall P. A., *J Pathology* 172:1–4 (1994).

A second class of tests for identifying gene mutations in patient samples makes use of nucleic acid probes which specifically hybridize with the portion of the gene containing the mutation site. Probe-based tests have high accuracy (few false negatives) and specificity (few false positives) for the specific mutation. A drawback to probe-based tests, however, is this very specificity which requires a priori detailed knowledge of the mutation being tested for, requires a unique set of reagents for each mutation, and may result in the failure to detect new types of mutations. Because of these drawbacks, this class of tests has also been criticized by some as being inadequate for meeting the diagnostic and screening challenges of the future. Ewanowich et al., *J. Clin. Microbiol.* 31:1715–25 (1993); Hatcher et al., *Prenat. Diagn.* 13:171–7 (1993); Bull et al., *The Lancet* 340:1360 (1992).

A third class of tests obtains the full sequence of the DNA for a particular gene recovered from the sample. Erickson, D., *Scientific American* 267:116 (1992). Rather than infer a diagnosis from indirect probe or protein tests, these tests read the DNA sequence of the gene of interest base by base. This method, which is known as Sequence-Based Diagnosis or SBD has the advantage of near 100% accuracy and 100 specificity. The disadvantage of this method, however, is the cost (approximately $1.00 per base) which effectively renders the method unavailable for screening applications, and even for many diagnostic applications.

It is an object of the present invention to provide a method for testing for mutations in DNA from a patient sample that meets the challenge of providing accurate, specific and yet cost effective diagnosis and targeted screening for the ever growing number of diseases associated with mutations in the genetic code.

SUMMARY OF THE INVENTION

This and other objects of the invention are achieved by a method in which a hierarchy of at least two assay techniques is utilized. This first assay in the hierarchy is selected to provide a highly specific test for the existence of the disease-associated mutation, although the accuracy of the test need not be high. The final assay in the hierarchy is selected to provide a highly accurate and highly specific test for the existence of the disease associated mutation. Intermediate tests of progressively greater accuracy may also be included in the hierarchy.

Once the hierarchy has been selected for a given mutation-associated disease, the patient sample is analyzed first using the lowest accuracy assay in the hierarchy. If the result of the first assay is negative for the presence of a disease-associated mutation, then the next assay in the hierarchy is performed. This process is repeated until the final assay has been performed on all samples which gave negative results when tested by all less-accurate assays in the hierarchy.

A major advantage of the claimed method as described above is the ability to dramatically reduce the per-sample cost of targeted genetic screening and diagnosis. By utilizing methods of progressively greater accuracy and cost only when the increased accuracy is actually needed, the reliability which was thought to be available only by extremely costly method of sequence-based diagnosis can be achieved at average per-patient costs that are a fraction of the cost normally associated with performing a sequence-based diagnosis.

BRIEF DESCRIPTION OF THE DRAWINGS

FIG. 4 shows a sub-hierarchy useful in testing for mutations in the RB1 gene.

DETAILED DESCRIPTION OF THE INVENTION

Figure 1:
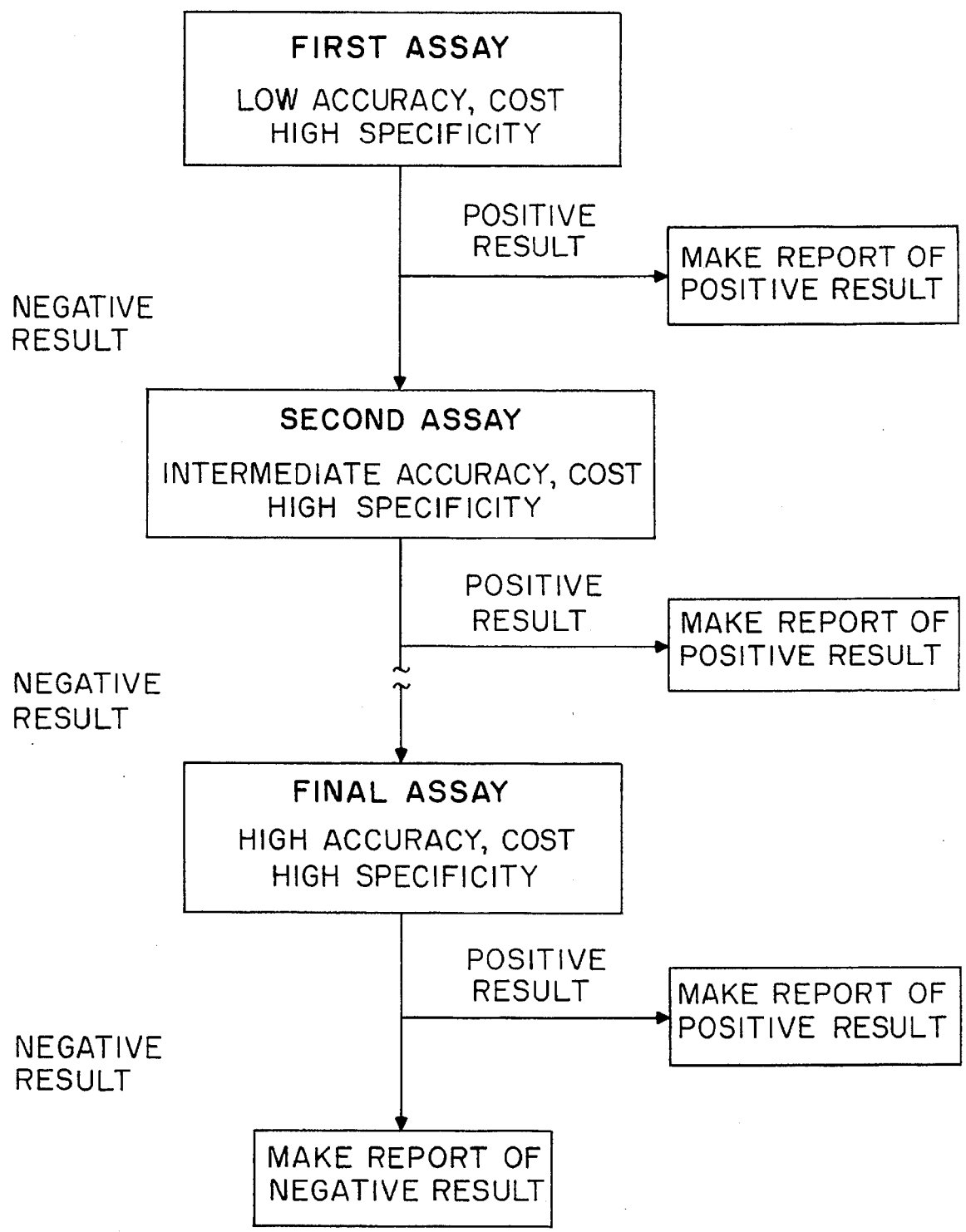
FIG. 1 shows a flow chart of the fundamental concept of the present invention.

The present invention involves the use of a structured diagnostic approach to the identification of disease-associated mutations in patient samples. The fundamental concept of the invention is the utilization of a testing hierarchy composed of a plurality of assay techniques of increasing accuracy (and thus generally of increasing cost) as a targeted screening or diagnostic method for evaluation of patient samples. The lowest assay technique in the hierarchy is applied to all samples submitted for testing. If a positive result is obtained in the first assay, a report is made indicating a positive result for the sample. If a negative result is obtained, the sample is tested using the next assay up in the hierarchy. This process is repeated until the highest level of the hierarchy has been reached.

In selecting assays suitable for use in the claimed invention, the meaning of several terms is of importance. As used in the specification and claims of this application, the term "specificity" relates to the incidence of false positive results in a particular tests. A test which has "high specificity" has fewer than 1% false positive results, and thus rarely, if ever, gives an erroneous indication that a mutation is present, but may fail to detect the mutation in some or even many instances. In contrast, the term "accuracy" relates to the incidence of false negative results. A test which has "high accuracy" has fewer than 1% false negative results, and thus will rarely if ever miss the presence of a mutation, although it may provide an incorrect diagnosis for the presence of the mutation. Tests with higher specificity and accuracy, for example with an error rate of less than 0.1% may of course be used if the cost of such tests does not exceed the benefits of the better performance.

As used herein, the term "disease-associated mutation" refers to any mutations which leads to a non-functioning or defective gene product or to the failure to produce any gene product from the mutated gene. Such mutations may be point mutations (i.e., mutations in which one or more bases within the nucleic acid sequence have been replaced by a different base), insertion mutations (i.e., mutations in which the total length of the gene of interest has been increased by the insertion of one or more bases), deletion mutations (mutations in which the total length of the gene of interest has been decreased by removal of one or more bases) and inversion mutations (mutations in which a region of two or more bases has been rotated 180 degrees), or combinations of these.

As used herein, the term "targeted screening" refers to screening tests performed on individuals who as a result of family relationship, exposure to hazardous environments or other factors have been identified as being within a risk group for a particular form of genetic disease.

The tests forming the hierarchy in accordance with the invention are selected from among tests of high specificity, where the accuracy of the tests gets progressively greater. The specific tests which are most suitably selected depend on a number of factors. To illustrate the selection criteria for the assay hierarchy, several representative examples will be considered.

FIG. 1 shows a suitable hierarchy for use in testing for a disease-associated mutation that results in the production of a defective gene product normally resulting from one of several previously identified point mutations. As shown, the samples from a plurality of patients are first tested for a disease-associated mutation in a gene of interest by first performing an immunoassay on a portion of the sample obtained from each patient. Such a test will generally be selected to provide a positive reaction in the presence of gene-product of a mutant gene. The immunoassay is selected to be highly specific such that any positive result is a reliable indicator of the existence of the disease-associated mutation, but need not be highly accurate.

Samples from patients that had negative immunoassay results are next tested using a probe-based assay. In general, the probe-based assay will utilize at least one oligonucleotide probe which specifically and selectively hybridizes with the gene of interest in its mutated form. Thus, the formation of a duplex nucleic acid hybrid containing the nucleic acid probe is indicative of the presence of the mutation in the gene of interest. Again, because of the high specificity of probe-based tests, any positive result may be relied upon as an indicator of the presence of the disease-associated mutation being tested for.

Samples for which both the immunoassay and the probe-based test are negative are further analyzed in accordance with the invention by determining the sequence of DNA in at least a selected region of the gene of interest. The sequence is then compared with known sequences of normal (wild-type or polymorphic) or mutant forms of the gene of interest. This final step gives a result which unambiguously indicates not only whether a mutation is present, but the nature of the mutation as well.

A hierarchy of the type shown in FIG. 1 could be applied, for example, in the diagnosis of and targeted screening for p53 mutations which produces a defective gene product that is generally the result of one of several identified point mutations. Assays specific for p53 mutations will be used to facilitate further discussion of this embodiment of the invention, but it should be understood that the applicability of this embodiment of the hierarchy is not limited to detection of p53 mutations, and might for example, be applied to detection of k-Ras, APC, DCC, p16 and HLA mutations as well.

The procedures for raising antibodies against specific gene products are well described in the literature, for example in U.S. Pat. Nos. 4,172,124 and 4,474,893 which are incorporated herein by reference. Antibodies are normally raised which bind to portions of the gene product away from common mutation sites such that the same antibody binds to both mutant and normal protein. For p53, antibodies of this type are available commercially from a variety of companies, including BioGenex (Bp53-12) and Oncogene Science (1801). Preferred antibodies for use in this invention are monoclonal antibodies because of their improved predictability and specificity. It will be appreciated, however, that essentially any antibody which possesses the desired high level of specificity can be used, and that optimization to achieve high accuracy is not required.

The antibody raised against the defective gene product is added to a portion of the patient sample under conditions where an immunological reaction will occur if the defective gene product is present, and the sample is then evaluated to see if such a reaction has occurred. The specific method for carrying out this evaluation is not critical. Examples of suitable methods include enzyme-linked immunoassays (ELISA), described in U.S. Pat. No. 4,016,043, which is incorporated herein by reference; fluorescent enzyme immunoassay (FEIA or ELFA), which is similar to ELISA, except that a fluorogenic enzyme substrate such as 4-methylumbelliferyl-$\beta$-galactoside is used instead of a chrmogenic substrate, and radioimmunoassay (RIA).

From the evaluation of the first assay, the next step to be performed in the process is determined. If the result is positive, the high specificity of the test allows the generation of a report, either in the form of a printed report or an electronic communication, for example transmitted by electronic mail or facsimile. The report may also be in the form of an entry into a computerized patient record, which can be retrieved later by the patient's physician.

If the result of the immunoassay is negative, the possibility of a false negative test precludes reaching any firm conclusion on the existence of a mutation. In this case, the sample is retested using the next test in the hierarchy.

In the example of p53 where there are recognized sites of likely point mutations, a suitable second test is based on nucleic acid hybridization. Suitable probes for hybridization assays will overlap with the known mutation sites occurring at amino acids 175, 248 and 273 of the p53 protein, and can be synthesized to be complementary to either the normal nucleic acid sequence or to recognized mutations.

Probe-based tests in accordance with the invention can be any of several general types. One type of probe-based test makes use of amplification primers which flank the site of a possible mutation. The amplified DNA is then combined with a labeled oligonucleotide probe which binds specifically to a portion of the amplified DNA spanning the possible mutation site in either its mutant or wild-type form. The presence or absence of hybridization is detected, and indicates the presence or absence of a mutation.

Numerous variations on this basic method are known and can be used in the practice of the present invention. For example, the amplified DNA may be made using biotinylated primers which facilitate immobilization of the amplified DNA and thus the separation of unbound labeled probe from the amplified DNA. A panel of probes specific for various known mutations can be immobilized as an array on a support, in a manner which has been used for HLA typing.

Prior to the testing of a sample using the direct hybridization method described above, the nucleic acids in the sample may be selectively amplified using a technique such as Polymerase Chain Reaction (PCR) amplification. This technique, which is described in U.S. Pat. Nos. 4,683,202 and 4,683,195, which are incorporated herein by reference, makes uses of two amplification primers each of which hybridizes to a different one of the two strands of the DNA duplex at a region away from the site of the mutation being tested for. Preferably, the primers will hybridize with non-coding portions of the DNA sequence (i.e., introns) located adjacent to the coding portion of the DNA sequence (exon-)containing the mutation site. Multiple cycles of primer extension, and denaturation are used to produce additional copies of DNA to which the primers can hybridize. In this way, the number of copies of the gene or exon of interest can be increased, thereby increasing both the specificity and the accuracy of the method.

PCR can also be used as part of a molecular weight probe assay to detect insertion or deletion mutations. In this procedure, the DNA in a sample is amplified using a defined pair of primers for each exon of the gene of interest, and the amplified product is analyzed using electrophoresis. If the primers are selected to bind to an intron adjacent to a mutation site of interest, the presence of insertion or deletion mutations can be determined by evaluating the molecular weight of the amplified portion of the gene. This procedure can advantageously be used in a "multiplexed" format, in which primers for a plurality of exons (generally from 4 to 8) are co-amplified, and evaluated simultaneously on a single gel. This is made possible by careful selection of the primers for each exon, the amplified fragment spanning the normal exon will have a length different from fragments spanning all other normal exons. The use of this technique has the advantage of detecting both normal and mutant alleles in heterozygous individuals. Furthermore, through the use of multiplexing it can be very cost effective.

Alternatively, PCR primers which bind specifically to mutated exons can be employed in the amplification to detect either key point mutations as well as insertion and deletion mutations. In this case, product will only be observed in the electrophoresis gel if hybridization of the primer occurred. Thus, the appearance of amplification product is an indicator of the presence of the mutation, while the length of the amplification product may indicate the presence of additional mutations.

A further type of test is one which does not require PCR amplification. In these tests, a probe specific for a DNA sequence is made with an RNA linker flanked by DNA. One end of the probe is labeled. The probe is mixed with the target DNA at the temperature which allows the full length probe to hybridize to the target. In the mix is the enzyme RNase H, which specifically cleaves RNA in RNA:DNA hybrids, but not single stranded RNA. As the temperature is lowered, the enzyme becomes active and if the probe has found a target it will be cleaved by the enzyme. The temperature is then raised and the any cleaved probe (which is now shorter) will melt off the target, opening up a space for more full length probe to bind. This process is repeated to build up a sufficient amount of cleaved probe to be detectable by gel electrophoresis.

In the foregoing test formats, the type of detectable label employed is not critical. Suitable labels include radioactive isotopes, for example $^{35}S$, luminescent labels such as fluorescein, ABC kits or chemiluminescence.

Evaluation of gene products by immunoassay and nucleic acid hybridization probe-based assays are properly considered "indirect" methods, because the presence or absence of a mutation is inferred from the interaction of the sample with a test reagent. Other indirect methods of testing for may also be employed in the method of the invention as one test in the hierarchy of test methods, either in place of in addition to immunoassay or probe-based methods. For example, Single-Stranded Conformational Polymorphism (SSCP) which relies on the shape of the folded gene, Restriction Fragment-Length Polymorphism (RFLP) which relies on the length of specific DNA fragments produced using restriction endonucleases, or heteroduplex DNA detection can be utilized in circumstances where that offer the requisite level of specificity. Such methods are described in U.S. Pat. Nos. 4,582,788, 4,683,194, and 5,227,292, which are incorporated herein by reference.

The final test in the hierarchy of the invention should be a test which provides both high specificity and high accuracy. A suitable test for this purpose is the determination of the sequence of the gene or exon of interest.

DNA sequencing may be carried out using automated systems designed for laboratory application. Methods and apparatus for sequencing of DNA are described in U.S. Pat. Nos. 4,811,218; 4,823,007; 5,062,942; 5,091,652; 5,119,316 and 5,122,345, which are incorporated herein by reference. The general methodology employed in these systems involves amplifying (for example with PCR) the DNA fragments of interest; combining the amplified DNA with a sequencing primer which may be the same as or different from the amplification primers; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. Analysis of fragments may be done by electrophoresis, for example on a polyacrylamide gel.

While such methods, which are based on the original dideoxy-sequencing method disclosed by Sanger et al., are useful in the present invention, the final assay is not limited to such methods. For example, other methods for determining the sequence of the gene of interest, or a portion thereof, may also be employed. Alternative methods include variations of the dideoxy method and methods which do not rely on chain-terminating nucleotides at all such as that disclosed in U.S. Pat. No. 4,971,903, which is incorporated herein by reference.

Figures 2, 3:
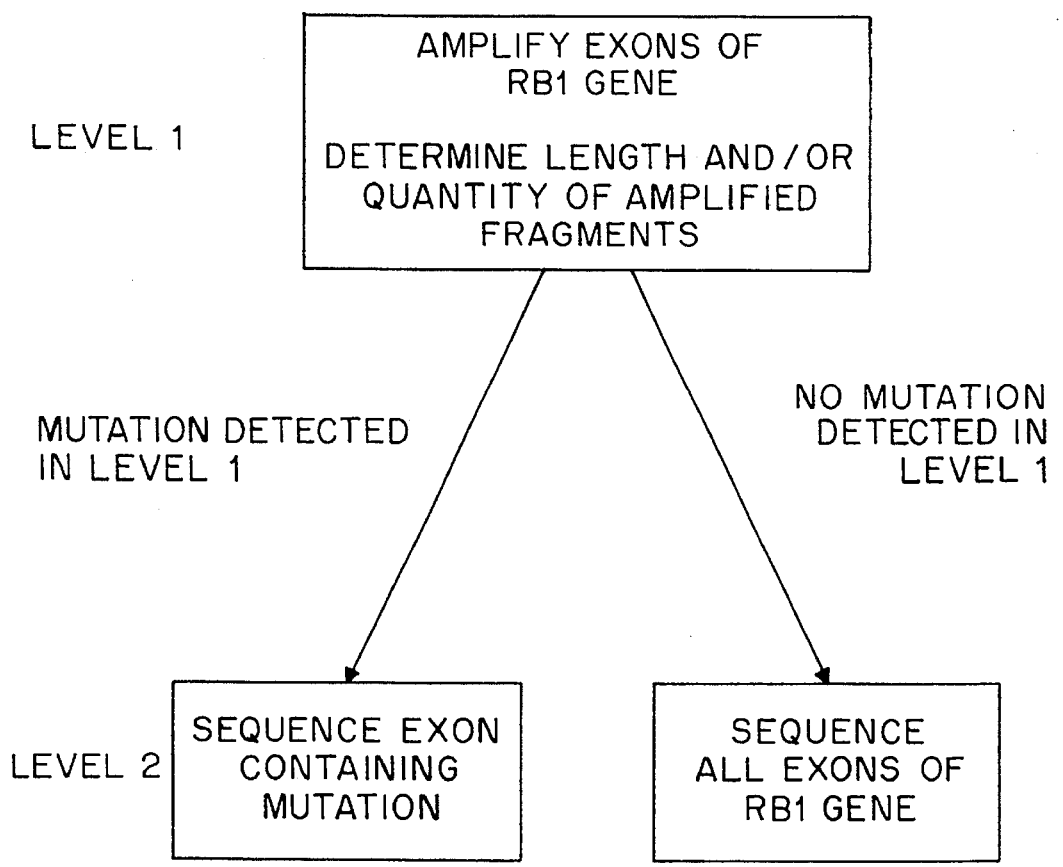
FIG. 2 shows a cost evaluation comparing the cost of a three-level hierarchy of the type shown in FIG. 1.
FIG. 3 shows a hierarchy suitable for diagnosis and targeted screening for mutations in the RB1 gene.

FIG. 2 shows a cost evaluation comparing the cost of a three-level hierarchy of the type shown in FIG. 1 compared to the cost of using sequence based diagnosis on all individuals. As can be seen, the potential savings using the method of the invention are substantial.

To further exemplify the method of the invention, FIG. 3 shows a hierarchy suitable for diagnosis and targeted screening for mutations in the RB1 gene. Mutations in this gene are associated with the initiation of an eye cancer known as retinoblastoma and are implicated in the progression of other cancers such as lung cancer and breast cancer.

Disease-associated mutations in the RB1 gene generally do not produce a defective gene product, but rather result in a failure to produce the RB protein. Since this protein is involved in the regulation of cell division, failure to produce RB protein results in uncontrolled cell division and tumor formation. Furthermore, disease-associated mutations in the RB gene are highly diverse, and are often unique from one family to the next. This makes assay procedures for RB1 mutations a particular challenge.

Because the result of a mutation in the RB1 gene is normally the absence of the normal gene product rather than a defective gene product, immunoassays are of little utility in detection of RB1 mutations, although quantitative immunoassay can be used in some cases to detect heterozygosity, which result in production of ½ the normal amount of protein. Bignon et al., *Genes Der.* 7:1654–1662 (1993). Antibodies for this purpose, if desired, can be raised by normal techniques as described in Lee, et al., *Nature* 329:642–645 (1987). Alternatively, synthetic antigens which mimic parts of the RB gene product's structure can be used to stimulate antibody production. Such antibodies are described, for example, in International Patent Publications Nos. 92/12807, 89/06703, and European Patent Application No. 390 530.

The preferred method for detection of RB mutants and similar mutants, however, omits the immunoassay, and proceeds directly to an assay designed to detect insertion or deletion mutations. As described in more detail in concurrently filed U.S. patent application No. 08/271,942, incorporated herein by reference, this is particularly useful in the case of retinoblastoma where approximately 50% of the mutations involve insertions or deletions of one base pair or more.

The method for identification of mutations in the RB1 gene is based upon a hierarchical approach in which a sample derived from a patient diagnosed with retinoblastoma is first tested with a test of moderate accuracy but high specificity, that is a test which detects about 50% of all mutations (i.e., about 50% false negatives), but essentially never gives a false positive reading. A sample which exhibits a negative result is thereafter subjected to a more costly, but more accurate test to determine if a mutation is present. By eliminating this test from over half of the samples, however, the average cost of the test goes down without sacrificing analytical performance.

In the case of testing for mutations in the RB1 gene, the hierarchy preferably consists of two levels. Level 1, as shown in FIG. 3, involves a test performed on all patient samples. In this test, one or more exons of the RB1 gene are individually amplified and the lengths of the amplified fragments are determined. If there is a variance between the length of any amplified exon, and the normal length of that exon, this is an indication of an insertion or deletion mutation in that exon.

The number of exons tested in Level 1 of the hierarchy is a matter of choice for the user. For example, it has been observed that disease-associated mutations in the RB1 gene rarely occur in exons 5, 25, 26 and 27. It may therefore be desirable to test these exons last, after testing other exons to see if a mutation sufficient to cause the disease is detected, before incurring the expense to test these less likely exons. In testing these other exons, the user may choose to test them one at a time, or in one multiplexing group at a time. Alternatively, the user may choose to test all exons simultaneously at the first level of the hierarchy.

When a mutation is detected in level one of the hierarchy, it is not necessary to perform additional tests on the patient sample to complete the identification process. Preferably, however, the sequence of the mutated exon will be determined as part of the second level of the hierarchy to confirm that the mutation detected can in fact be a cause of the observed disease.

If no mutation is detected in the first level of testing, the second level of tests is performed. This involves determining the sequence of the exons to locate the mutation. Because sequencing is expensive, however, it may be desirable to use a sub-hierarchy within this level of testing to reduce the likelihood of having to sequence all of the exons. In this case, a suitable sub-hierarchy is shown in FIG. 4. In accordance with this sub-hierarchy, the first exons sequenced (Level 2A) are those which are easy to sequence and which have been the site of other disease-associated mutations. Next, if no mutation which could result in retinoblastoma is found, exons are sequenced which are hard to sequence and which have been the site of other disease-associated mutations (Level 2B). The third level of the sub-hierarchy includes exons which are easy to sequence but which have never been shown to contain a disease-associated mutation. (Level 2C). Finally, exons are sequenced which are hard to sequence but which have never been shown to contain a disease-associated mutation (Level 2D).

The primers used to amplify the sample DNA for the first test in the hierarchy are oligonucleotides of defined sequence selected to hybridize selectively with particular portions of the RB1 gene. Each primer has bound to it a detectable label. A preferred example of such a label is fluorescein, which is a standard label used in nucleic acid sequencing systems using laser light as a detection system. Other detectable labels can also be employed, however, including other fluorophores, chemiluminescent labels, radio-labels, chemical couplers such as biotin which can be detected with streptavidin-linked enzymes, and epitope tags such as digoxigenin detected using antibodies available from Boehringer-Mannheim.

While considerable variation is possible in the sequence of the primers used in amplifying the exons during the first step in the method of the present invention, the primers used in amplification and the conditions of the amplification are preferably optimized for use in the present invention. Looking first at the primers used, it will be understood that in order to avoid the possibility of false positive results the primer pair, i.e., the combination of the 5'-primer and the 3'-primer for any given exon must be unique to the RB1 gene so that only the RB1 gene will be amplified. This means that the primer sequences will be generally somewhat longer than the minimum which can be used as an amplification primer. Preferred primers are from 18 to 23 nucleotides in length, without internal homology or primer-primer homology. It is also desirable for the primers to form more stable duplexes with the target DNA at the primer's 5'-ends than at their 3'-ends, because this leads to less false priming. Stability can be approximated by GC content, since GC base pairs are more stable than AT pairs, or by nearest neighbor thermodynamic parameters. Breslauer et al., "Predicting DNA duplex stability from base sequence", *Proc. Nat'l Acad. Sci. U.S.A.* 83:3746–3750 (1986). In addition, to ensure complete amplification of each exon, the two primers of a pair are preferably selected to hybridize in the introns immediately flanking the exon to be amplified using the primer pair.

Additional factors apply to the selection of primers for multiplexed amplification of exons. These factors are discussed in Rylchik, W., "Selection of Primers for Polymerase Chain Reaction", in *Methods in Molecular Biology, Vol. 15: PCR Protocols: Current Methods and Applications,* White, B. A. ed., Humana Press, Totowa, N.J., 1993. Briefly, applying these factors, primer pairs are selected by position, similarity of melting temperature, internal stability, absence of internal homology or homology to each other, i.e., they won't stick to each other or to themselves, and the 3'-end will not form a stable hairpin loop back on itself.

Thus, in the present case, the goal is to have sets of primer pairs with approximately the same thermal profile, so that they can be effectively coamplified together. This goal can be achieved by having groups of primer pairs with approximately the same length and the same G/C content. In addition, it is preferred that the length of the gene region between the primer binding sites on a normal RB1 gene differ for each exon to be multiplexed as a group. Differences of only one base in length are sufficient, provided a high resolution gel capable of resolving one base differences is used in analyzing the amplification products. However, greater differences in length are preferred.

In addition to the selection of suitable primers, best results in the fragment length analysis are obtained if the amplification reaction is carried out for a limited number of amplification cycles. It will be understood, that the more cycles of amplification are carried out, the more of the desired product will be made and thus the easier its detection will be. It should also be recognized, however, that during the initial cycles (generally the first 20–25 cycles), the amount of DNA of the desired sequence doubles in each cycle, while thereafter the yield of desired product drops off. For maximum effectiveness in the method of the present invention, the amplification of the exons in the patient sample should be carried out only for a number of cycles during which doubling of DNA is still being achieved. Such amplification is referred to in the specification and claims hereof as "quantitative" amplification.

After amplification of the exons of RB1 gene, the amplification products are analyzed electrophoretically using a sequencing gel. Preferred gels will have a resolution of one base pair, so that one base deletions or insertions, which are relatively common in cases of retinoblastoma, can be identified. A suitable gel is a polyacrylamide gel of the type recommended for use with the Pharmacia A.L.F. Sequencer.

The type of detector system used to analyze the gel depends on the type of label employed on the amplification primers. For example, in the case of radio-labeled primers, the gel might be analyzed by autoradiography. The preferred labels, however, are fluorophores which are detected using photodiodes, photomultipliers or other light sensitive devices.

Figure 5:
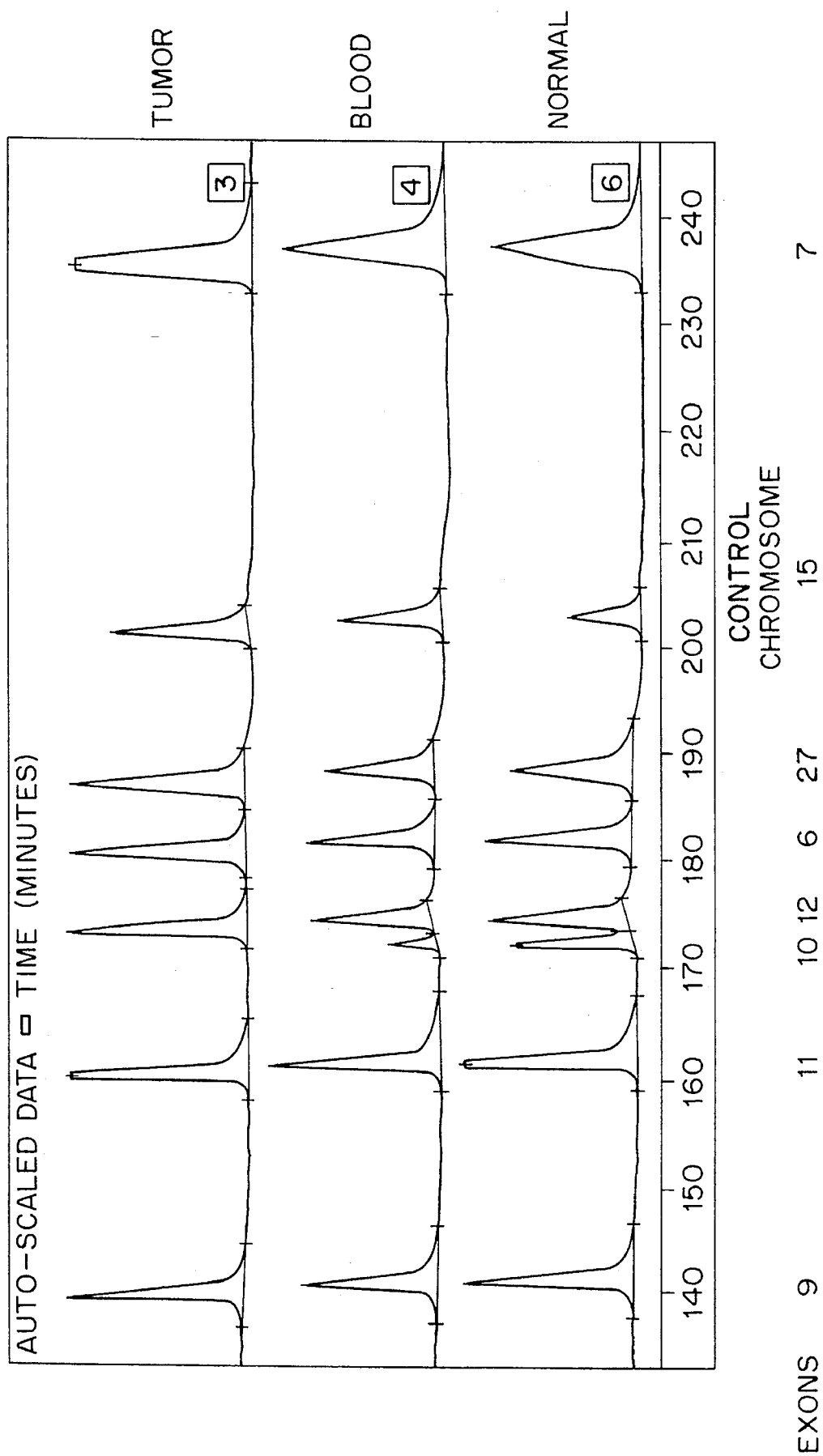
FIG. 5 shows a sample output of a Pharmacia A.L.F. Sequencer using fluorescein-labelled primers to monitor the length of amplification products.

FIG. 5 shows a sample output of a Pharmacia A.L.F. Sequencer using fluorescein-labelled primers. Each peak in the output corresponds to a single-stranded fluorescein-labeled amplified DNA product from a PCR reaction migrating in the gel. Each exon of the RB1 gene and a control exon from a gene on chromosome 15 unrelated to RB1 migrate at a different rate. By comparison of the peaks from the patient samples to those of the wild type, it can be determined that a mutation exists, in this case the complete deletion of exon 10 from one allele, or the deletion of part of an exon and one of the priming sites. In a sample from the patient's tumor tissue, the mutation is homozygous (no exon 10), while in the blood of this patient, the exon 10 peak is reduced by 50% indicating that this patient carries the mutation in his or her somatic tissue, and therefore probably in their germline. The deletion of exon 10 leads to a severely truncated RB1 protein lacking many of the regions required for proper function, therefore it can be safely assumed that this is the disease causing mutation.

The second level of the hierarchy calls for the sequencing of one or more exons of the RB1 gene. Preferably, this sequencing process is performed on amplified DNA. The primers used in the pre-sequencing amplification can have the same sequence as those used in the first level of the test hierarchy, or they may be different. In either case, however, it is preferred that instead of the detectable labels used on the primers in the first level amplification, during pre-sequencing amplification one of the primers of each pair will be modified to facilitate recovery. For example, one primer of each pair may be biotinylated so that it can be recovered by binding to a streptavidin-coated support.

One of the crucial parameters for a successful tissue transplant is to have HLA types match as closely as possible. Since the chance of rejection decreases as the match gets closer, the more accurate the determination of the HLA type, the more likely a successful transplant. Direct reading of the DNA sequence of the HLA genes would therefore be advantageous. The large number of potential donors needing to screened, however, makes direct sequencing using present technology unfeasible. Accordingly, a stepwise, hierarchical screening approach in accordance with the present invention is useful in determining HLA types.

The first step in an HLA hierarchical typing is a serological evaluation performed on the blood of potential donors and recipients. Antibodies are available which react with (i.e., bind to) specific groups of HLA class I molecules on the surface of the lymphocytes found in whole blood. These are highly specific tests for the HLA class I groups, but they have low accuracy and are unable to distinguish one member of the group from another. These tests can also be done rapidly and economically on a very large number of potential donors. The donors are then grouped according to their serological classification.

Potential transplant donors and recipients are then tested to determine their HLA class II type using a probe-based test with either the sequence specific primer (SSP) or allele specific oligonuceltoide (ASO) approaches described above. These tests are performed on DNA isolated from peripheral blood lymphocytes (PBL) using sets of probes for particular HLA class II sub-types. Examples of suitable probe-based tests for HLA typing are found in U.S. Pat. No. 4,582,788 which is incorporated herein by reference.

Based upon the class I and class I types are known for each potential donor and recipient, the field of possible donors for a given recipient is narrowed. The HLA genes of these selected possible donors and the recipient are then sequenced using only primers specific for the sub-types found to be present in the prior tests. In this way, an exact sequence match of the HLA genes can be found from a large number of potential donors at a reasonable cost.

A further example of a disease which is suitably diagnosed using the hierarchical method of the invention is cystic fibrosis. Cystic fibrosis (CFTR) was once believed to be the result of only a few mutations which were thought to have arisen many generations ago and been carried in the population ever since. With the cloning of the gene and detailed searches for mutations, however, we now know this to be false. Although there are a few mutations which are very prevalent, the number of different mutations found so far is in the hundreds, and the rate at which they are being found shows no sign of decreasing. This makes it difficult to provide accurate genetic counseling for cystic fibrosis at a reasonable price using conventional single test strategies.

Depending on the genetic background of the patient, there are a small number of known mutations (generally less than 20) which will account for about 90% of the CFTR mutations found in that group. For example, 17 mutations account for 94% of the CFTR mutant chromosomes within the Belgian population. The remaining mutations are found at very low frequency, i.e., less than 0.1%. Thus, cystic fibrosis is ideally suited to hierarchical targeted screening.

As with RB, only one affected member from each family is screened initially for the identification of the mutation. DNA from the PBLs of the affected family member is tested using a set of DNA probes which provide the greatest information for their genetic background, or if the genetic background is unknown a set of probes which is most informative over all genetic backgrounds. These probes can be of the type which only hybridize to a specific allele (ASO), they can be half of a PCR primer pair which will only amplify a specific allele (SSP) or they can amplify a region of the gene containing a mutation which alters a restriction endonuclease recognition site (PCR-RFLP). The presence of a bound probe, an amplified product or an expected restriction site is then evaluated to see if one of the most common mutations is present.

Samples which fail to show a mutation in the first step of the hierarchical analysis are tested further using tests of higher accuracy. For example, fragment length analysis of each amplified exon can be performed in the manner discussed above for RB mutations to find small and large insertions or deletions. These same fragments might also be analyzed by heteroduplex formation. This technique takes advantage of the fact that the mobility of perfectly matched duplex DNA (homoduplex) on a polyacrylamide gel is different from the mobility of duplex DNA (heteroduplex) that is not perfectly matched. Since the blood of a heterozygous patient will carry both the normal and mutant allele, amplified DNA can be denatured and then reannealed. This will result in the formation of the original homoduplexes, but also in the formation of heteroduplexes if there is a mutation in one allele. The ronald sample is then separated by gel electrophoresis and shifts in mobility are noted. Other methods such as single-stranded conformational polymorphism (SSCP) or denaturing gradient gel electrophoresis (DGGE) can also be used to detect variation within a gene fragment.

Once an exon is identified as containing a mutation, that exon is tested in other at-risk family members as in the case of the RB gene discussed above. Further, the sequence of the identified exon may be determined to confirm the test results. If no mutation is detected in the affected individual using the middle level tests of the hierarchy, the CFTR gene is sequenced exon-by-exon until the mutation is located.

From the foregoing discussion, it will be apparent that the hierarchical method of the present invention can be applied to a wide variety of diseases and conditions. The basic techniques described herein can be readily adapted to other disease and conditions not specifically discussed here.

EXAMPLE 1

A blood sample is received from a patient diagnosed as suffering from retinoblastoma. Genomic DNA is prepared from the samples using a Qiagen QIAamp Kit according to the accompanying directions. Briefly, an aliquot of the sample, or a lymphocyte-containing fraction thereof, is combined with Proteinase K, mixed, and allowed to incubate to lyse the cells. Ethanol is added and the lysate is transferred to a QIAamp spin column from which DNA is recovered after several washings.

The genomic DNA is next amplified in five sets using multiplexing primers. Each 50 µl multiplexed PCR reaction contains 0.5 µg genomic DNA, 150 ng of each primer, 3.6 mM each dNTP, 42.5 µg Bovine Serum Albumin, 5 units Taq polymerase in a buffer containing 10% DMSO, 16 mM $(NH_4)_2SO_4$, 6.7 mM $MgCl_2$, 6.8 µM EDTA (pH 8.0) and 1 mM β-mercaptoethanol. The reaction mixture was initially incubated at 94° C. for 5 minutes and then subjected to an appropriate number of cycles of PCR in a Perkin-Elmer/Cetus thermocycler as follows:

denaturation 94° C., 30 seconds annealing 53° C. or 55° C., 30 seconds extension 72° C., 4 minutes—final extension 7 minutes.

In the first set, exons 2, 3, 5, 13 and 25 are amplified, together with a control sequence which is a DNA segment from chromosome 15, unrelated to RB1, for 18 cycles. The primers, one of each pair being labeled with fluorescein at the 5'-end, are

| exon | 5'-primer | 3'-primer |
| --- | --- | --- |
| 2 | ACTGTGTGGT ATCCTTATTT TG [SEQ. ID. NO. 1] | ATAGTGATTT GAAGTTGGTT TTA [SEQ. ID. NO. 2] |
| 3 | ATACAGTTTT AACATAGTAT CCA [SEQ. ID. NO. 3] | AAGTCTATTG AGAGGAAAAT CC [SEQ. ID. NO. 4] |
| 5 | CTACTATGAC TTCTAAATTA CG [SEQ. ID. NO. 5] | TCAAGATGTT TGAGATTATT CC [SEQ. ID. NO. 6] |
| 13 | TGCTTATGTT CAGTAGTTGT G [SEQ. ID. NO. 7] | TAATGGGGTG GGAGGTAGTT T [SEQ. ID. NO. 8] |
| 25 | TCAAACTATA ACTTGAGGTT GC [SEQ. ID. NO. 9] | AAAGAAATTG GTATAAGCCA GG [SEQ. ID. NO. 10] |
| con | CTCACCCGCA CCTAAGTTT [SEQ. ID. NO. 11] | CCAGGATGAG AGCGGAGGC A [SEQ. ID. NO. 12] |

These primers result in amplified products with normal fragment lengths of 410, 262, 170, 461 and 316 base pairs, respectively. The control sequence produces a fragment having a length of 325 base pairs.

In the second set, exons 1, 8, 18, 21, 22, and 23 are amplified, together with the same control sequence, for 18 cycles. The primers, one of each pair of which is labeled with fluorescein, are

| exon | 5'-primer | 3'-primer |
|---|---|---|
| 1 | GCCCCAGTTC CCCACAGAC [SEQ. ID. NO. 13] | ACCCCTCGCC CAAGAACCC [SEQ. ID. NO. 14] |
| 8 | TCTAATGAAA CCTAARAAGT A [SEQ. ID. NO. 15] | TGCTCATAAC AAAAGAAGTA [SEQ. ID. NO. 16] |
| 18 | TTTTTGTGTG TGGGAAGTAC A [SEQ. ID. NO. 17] | ATTCTATTCC CTACAGTTTC TT [SEQ. ID. NO. 18] |
| 21 | GGCTAAAAGA AAGAAAATGG [SEQ. ID. NO. 19] | TTACCTATGT TATGTTATGG [SEQ. ID. NO. 20] |
| 22 | TATGTGCTTC TTACCAGTCA AA [SEQ. ID. NO. 21] | GGAGTCATTT TTGTTGGTGT TG [SEQ. ID. NO. 22] |
| 23 | AATCTAATGT AATGGGTCCA CC [SEQ. ID. NO. 23] | ATCAAATAA TCCCCCTCTC AT [SEQ. ID. NO. 24] |

These primers result in amplified products with normal fragment lengths of 591, 366, 418, 251, 496 and 283 base pairs, respectively.

In the third set, exons 6, 7, 9, 10, 11, 12 and 27 are amplified, together with the same control sequence, for 20 cycles. The primers, one of each pair being labeled with fluorescein, are

| exon | 5'-primer | 3'-primer |
|---|---|---|
| 6 | AAAGAAACAC CCAAAAGATA [SEQ. ID. NO. 25] | TAATAAGCCA AGCAGAGAAT GA [SEQ. ID. NO. 26] |
| 7 | TTATGGATAT ACTCTACCT GC [SEQ. ID. NO. 27] | CCTCCATTTG TTGTATTTTG AC [SEQ. ID. NO. 28] |
| 9 | TCAAGAGTCA AGAGATTAGA [SEQ. ID. NO. 29] | ATTATCCTCC CTCCACAGTC TC [SEQ. ID. NO. 30] |
| 10 | GTGCTGAGAG ATGTAATGA [SEQ. ID. NO. 31] | TATCTAAAGC AAATCAATC [SEQ. ID. NO. 32] |
| 11 | TGAGACAACA GAAGCATTAT [SEQ. ID. NO. 33] | TGAACAAATC TGAACATA T [SEQ. ID. NO. 34] |
| 12 | CTCCCTTCAT TGCTTAACAC AT [SEQ. ID. NO. 35] | AAAAGCAAGA AAAGATTATG G [SEQ. ID. NO. 36] |
| 27 | ACTTACCCAG TACCATCAAT [SEQ. ID. NO. 37] | TCAAGTGGCT TAGGAATCAC CC [SEQ. ID. NO. 38] |

These primers result in amplified products with normal fragment lengths of 283, 423, 205, 264, 244, 270 and 297 base pairs, respectively.

In the fourth set, exons 4, 14, 20, 24 and 26 are amplified, together with the same control sequence, for 18 cycles. The primers, one of each pair being labeled with fluorescein, are

| exon | 5'-primer | 3'-primer |
|---|---|---|
| 4 | TTGAAAACGA AATAACAC [SEQ. ID. NO. 39] | ATAAAAAATC AGAGTGTAAC CC [SEQ. ID. NO. 40] |
| 14 | GTGATTTTCT AAAATAGCAG GC [SEQ. ID. NO. 41] | CCAGGATGAT CTTGATGCC [SEQ. ID. NO. 42] |
| 20 | GAAAAGAGTG GTAGAAAAGA GG [SEQ. ID. NO. 43] | TAACAAGTAA GTAGGGAGGA GA [SEQ. ID. NO. 44] |
| 24 | GTATTTATGC TCATCTCTGC [SEQ. ID. NO. 45] | GTGTTTGAAT AACTGCATTT GG [SEQ. ID. NO. 46] |
| 26 | CGAAAGCATC ATAGTTACTG [SEQ. ID. NO. 47] | ATATAACGAA AAACTTCTT GC [SEQ. ID. NO. 48] |

These primers result in amplified products with normal fragment lengths of 228, 227, 343, 206, and 203 base pairs, respectively.

In the fifth set, exons 15 and 16 are amplified together, along with exons 17, 19, the RB1 promoter region and the same control sequence, for 20 cycles. The primers, one of each pair being labeled with fluorescein, are

| exon | 5'-primer | 3'-primer |
|---|---|---|
| 15, 16 | CAATGCTGAC ACAAATAAGG TT [SEQ. ID. NO. 49] | CCCCCGACCA AAGAAACACA [SEQ. ID. NO. 50] |
| 17 | ACCTTTCTAC TGTTTTCTTT GT [SEQ. ID. NO. 51] | AAACACCTCT CACTAACAAT [SEQ. ID. NO. 52] |
| 19 | TGTATAATCT GTGATTCTTA GC [SEQ. ID. NO. 53] | GCAACATTAT CATTTCCATT TT [SEQ. ID. NO. 54] |
| PROM | CCCACCAGAC TCTTTGTA [SEQ. ID. NO. 55] | ACGTCCCCTG AGAAAAACCG GA [SEQ. ID. NO. 56] |

These primers result in amplified products with normal fragment lengths of 335, 371, 363, and 316 base pairs, respectively.

After amplification, the products from each amplification reaction are denatured and loaded onto a polyacrylamide sequencing gel in a Pharmacia A.L.F. automated sequencer. The single-stranded amplification products migrate through the gel at a rate determined by their length, and are detected using the fluorescence of the fluorescein label which was attached to the primers.

EXAMPLE 2

The process of selecting primers for use in the invention can be illustrated with reference to exons 4 and 6 of the RB1 gene. Two primer pairs have been identified for exon 4 and one primer pair has been identified for exon 6. Primer 4×5'-A is a 20-mer having the sequence ATATAGTAGT GATTTGATGT          [Seq. ID No. 57]

which is homologous to a region in the intron immediately adjacent to the 5'-end of exon 4 of the RB1 gene. This region starts 122 bases from the 5'-end of the exon and extends to the base which is 103 bases from the exon. The primer has a predicted melting temperature of 50° C.

Primer 4×3'-A is a 20-mer having the sequence

ATGACATAAA AAATCAGAGT          [Seq. ID No. 58]

which is homologous to a region in the intron adjacent to the 3'-end of exon 4 of the RB1 gene. This region starts 28 bases from the 3'-end of the exon and extends to the base which is 47 bases from the exon. This primer also has a melting temperature of 50° C.

Primer 6×5' is a 22-mer having the sequence

CACAAAAAGA AACACCCAAA AG          [Seq. ID No. 59]

which is homologous to a region in the intron adjacent to the 5'-end of exon 6 of the RB1 gene. This region starts 72 bases from the 5'-end of the exon and extends to the base which is 93 bases from the exon. The primer has a predicted melting temperature of 62° C.

Primer 6×3' is a 22-mer having the sequence

TAATAAGCCA AGCAGAGAAT GA          [Seq. ID No. 26]

which is homologous to a region of the intron adjacent to the 3'-end of exon 6 of the RB1 gene. This region starts 107 bases from the 3'-end of the exon and extends to the base which is 128 bases from the exon. The primer has a predicted melting temperature of 60° C.

These two primer pairs are effective for the amplification of exons 4 and 6 individually. They are not suited for use together in a multiplexed amplification, however, because the melting temperatures of the two pairs are too different. Furthermore, both of these primer pairs produce an amplification product which is 289 bases in length. Thus, the two primer pairs cannot be used with a common detectable label in a multiplexed reaction.

In order to amplify exon 4 and exon 6 in a single reaction, it is necessary to identify a different primer pair for one of the two exons which is compatible with the primer pair for the other exon. In this case, a suitable replacement is the primer pair identified by the inventors as 4×5'-B and 4×3'-B.

The primer 4×5'-B is a 22-mer having the sequence

AGTAGTGATT TGATGTAGAG CT          [Seq ID No. 60]

which is homologous to the region in the intron adjacent to the 5'-end of exon 4 that starts 98 bases from the 5'-end of the exon and extends to the base which is 119 bases from the exon. This primer has a melting temperature of 60° C. The primer 4×3'-B is a 22-mer having the sequence ATAAAAAATC AGAGTGTAAC CC          [Seq ID No. 40]

which is homologous to the region in the intron adjacent to the 3'-end of exon 4 starting 21 bases from the 5'-end of the exon and extends to the base which is 42 bases from the exon. This primer has a melting temperature of 58° C. Thus, these primers have melting temperatures which are much closer to the melting temperature of the exon 6 primers. Moreover, the amplification product has a length of 280 bases, which is 9 bases different from the amplification product of the exon 6 primers.

We claim:

1. A method for testing a plurality of patients for a disease-associated mutation in a gene of interest comprising the steps of:
   (a) performing an immunoassay on samples obtained from each of the plurality of patients by combining a portion of each sample with an antibody which forms an immunological reaction product by binding to a protein gene product of the gene of interest and monitoring for formation of the immunological reaction product, said antibody being selected to provide fewer than 1% false results indicating the presence of a mutation when combined with the protein gene product of the gene of interest, whereby the formation of an immunological product is indicative of the presence or absence of a mutation in the gene of interest;
   (b) performing a probe-based assay on each patient sample for which the results of the immunoassay did not indicate the presence of the mutation, but not on those samples for which the immunoassay indicated the presence of the mutation by combining a second portion of each patient sample with a nucleic acid probe which specifically and selectively hybridizes with the gene of interest in either its mutated or wild-type form, whereby the formation of a duplex nucleic acid hybrid containing the nucleic acid probe is indicative of the presence or absence, respectively, of the mutation in the gene of interest; and
   (c) determining the sequence of DNA in at least one selected region of the gene of interest on each patient sample for which the results of the probe-based assay did not indicate the presence of the mutation and comparing the sequence determined with known sequences of normal or mutant forms of the gene of interest.

2. A method according to claim 1, wherein the antibody binds to the protein gene product of the wild-type gene of interest, and the observation of immunological product at levels below a standard level which results from tests on homozygous wild-type samples is indicative of the presence of a mutation.

3. A method according to claim 1, wherein the antibody binds to a mutant gene product caused by the disease-associated mutation and not to the wild-type gene product of the gene of interest, and the observation of an immunological product is indicative of the presence of the disease associated mutation.

4. A method according to claim 1, wherein the sequences of a plurality of regions in the gene of interest are determined.

5. A method according to claim 4, wherein the sequences of the plurality of regions are determined in at least two phases in which regions having a greater incidence of disease-associated mutations in a population group to which the patient belongs are tested before regions having a lower incidence of mutations.

6. A method for testing a plurality of patients for a disease-associated mutation in a gene of interest comprising the steps of:
   (a) performing an immunoassay on samples obtained from each of the plurality of patients by combining a portion of each sample with an antibody which forms an immunological reaction product by binding to a protein gene product of the gene of interest and monitoring for formation of the immunological reaction product, said antibody being selected to provide fewer than 1% false results indicating the presence of a mutation when combined with the protein gene product of the gene of interest, whereby the formation of an immunological product is indicative of the presence or absence of the mutation in the gene of interest; and
   (b) performing a probe-based assay on each patient sample for which the results of the immunoassay indicated the absence of a mutation, but not on those samples for which the immunoassay indicated the presence of the mutation by combining a second portion of each patient sample with a nucleic acid probe which specifically and selectively hybridizes with the gene of interest in either its mutated or wild-type form, whereby the formation of a duplex nucleic acid hybrid containing the nucleic acid probe is indicative of the presence or absence, respectively, of the mutation in the gene of interest.

7. A method for testing a plurality of patients for a disease-associated mutation in a gene of interest comprising the steps of:

(a) performing a probe-based assay on each patient sample by combining a portion of each patient sample with a nucleic acid probe which specifically and selectively hybridizes with the gene of interest in either its mutant or wild-type form, said probe-based assay providing essentially no false indications of the presence of a mutation, whereby the formation of a duplex nucleic acid hybrid containing the nucleic acid probe is indicative of the presence or absence of the mutation, respectively, in the gene of interest; and (b) determining the sequence of DNA in at least a selected region of the gene of interest on each patient sample for which the results of the probe-based assay did not indicate the presence of a mutation, but not on those samples for which the probe-based assay indicated the presence of the mutation, and comparing the sequence determined with known sequences of wild-type or mutant forms of the gene of interest.

8. A method for testing a patient sample for a disease-associated mutation in a gene of interest, comprising the steps of:

(a) selecting a hierarchy of molecular assay techniques comprising at least a first molecular assay and a final molecular assay, said first molecular assay being selected to provide a test for the existence of the disease-associated mutation with essentially no false results indicating the presence of a mutation, and said final molecular assay being selected to provide a test for the existence of the disease associated mutation with essentially no false results indicating the presence or absence of a mutation;

(b) analyzing the patient sample using the first molecular assay; and, if the result of the first molecular assay did not unambiguously indicate the presence of the disease-associated mutation, (c) analyzing the patient sample using the final molecular assay.

9. A method according to claim 8, wherein the first assay is an immunoassay.

10. A method according to claim 8, wherein the nucleic acid sequence of at least one region of the gene of interest is determined in course of performing the final assay.

11. A method according to claim 10, wherein the first assay is an immunoassay.

12. A method according to claim 8, wherein at least one assay in the hierarchy comprises the steps of quantitatively amplifying one or more exons of the gene of interest in the sample using primers complementary to intron regions immediately flanking each amplified exon; and determining the lengths of the amplification products for each amplified sample exon and comparing that length to the length of amplification products obtained when a wild-type gene is amplified using the same primers, whereby differences in length between an amplified sample exon and the corresponding amplified wild-type exon reflect the occurrence of an insertion or deletion mutation in the gene of interest in the sample.

13. A method according to claim 12, wherein the length of the amplification products is determined by electrophoresis on a sequencing gel.

14. A method according to claim 13, wherein the sequencing gel has a resolution of one base pair.

15. A method according to claim 14, wherein the sequencing gel is a polyacrylamide gel.

16. A method according to claim 12, wherein the primers are each coupled to a detectable label.

17. A method according to claim 16, wherein the detectable label is fluorescein.

18. A method according to claim 12, wherein a plurality of exons of the gene of interest are coamplified in a single amplification reaction.

19. A method according to claim 18, wherein the primer pairs for each coamplified exon are selected to have a common melting temperature and to produce amplification products having differing lengths.

20. A method according to claim 8, wherein the cost per sample for performing the first assay is less than the cost per sample for performing the final assay.

21. A method according to claim 8, wherein the hierarchy further includes an intermediate assay for detecting the presence of the disease-associated mutation which is performed after the first assay on samples for which the first assay did not indicate the presence of a mutation and before the final assay, and wherein the final assay is performed only if the intermediate assay did not indicate the presence of a mutation, said intermediate assay providing essentially no false positives, and fewer false negatives than the first assay.

22. A method according to claim 21, wherein the first assay is an immunoassay.

23. A method according to claim 22, wherein the intermediate assay is a nucleic acid hybridization probe-based assay.

24. A method according to claim 23, wherein the sequence of a region of a gene of interest is sequenced in course of performing the final assay.

25. A method for generating a report on the presence or absence of a disease-associated mutation in a patient sample, comprising the steps of:

(a) selecting a hierarchy of molecular assay techniques comprising at least a first molecular assay and final molecular assay, said first molecular assay being selected to provide a test for the existence of the disease-associated mutation with essentially no false results indicating the presence of a mutation and said final assay being selected to provide a test for the existence of the disease associated mutation with essentially no false results indicating the presence or absence of a mutation;

(b) analyzing the patient sample using the first molecular assay, and if the result of the first assay does not indicate the presence of a disease-associated mutation, (c) analyzing the patient sample using the final molecular assay; and (d) generating a report containing advice that the disease-associated mutation is present in the patient sample if a test result indicating the presence of the disease-associated mutation is obtained in any assay of the hierarchy, and advice that the disease-associated mutation is absent if a test result indicating the absence of a mutation is obtained in all of the assays in the hierarchy.

26. A method according to claim 25, wherein the report is a printed report.

27. A method according to claim 25, wherein the report is an electronic communication.

28. A method according to claim 25, wherein the report is a data entry in a computer record containing information about the patient.

29. A method according to claim 25, wherein the first assay is an immunoassay.

30. A method according to claim 25, wherein the nucleic acid sequence of at least one region of the gene of interest is determined in course of performing the final assay.

31. A method according to claim 28, wherein the first assay is an immunoassay.

32. A method according to claim 25, wherein at least one assay in the hierarchy comprises the steps of quantitatively amplifying one or more exons of the gene of interest in the sample using primers complementary to intron regions flanking each amplified exon; and determining the lengths of the amplification products for each amplified sample exon and comparing that length to the length of amplification products obtained when a wild-type gene is amplified using the same primers, whereby differences in length between an amplified sample exon and the corresponding amplified wild-type exon reflect the occurrence of an insertion or deletion mutation in the gene of interest in the sample.

33. A method according to claim 30, wherein the length of the amplification products is determined by electrophoresis on a sequencing gel.

34. A method according to claim 31, wherein the sequencing gel has a resolution of one base pair.

35. A method according to claim 32, wherein the sequencing gel is a polyacrylamide gel.

36. A method according to claim 30, wherein the primers are each coupled to a detectable label.

37. A method according to claim 34, wherein the detectable label is fluorescein.

38. A method according to claim 30, wherein a plurality of exons of the gene of interest are coamplified in a single amplification reaction.

39. A method according to claim 36, wherein the primer pairs for each coamplified exon are selected to have a common melting temperature and to produce amplification products having differing lengths.

40. A method according to claim 25, wherein the cost per sample for performing the first assay is less than the cost per sample for performing the final assay.

41. A method according to claim 25, wherein the hierarchy further includes an intermediate assay for detecting the presence of the disease-associated mutation which is performed after the first assay on samples for which the first assay did not indicate the presence of a mutation and before the final assay, and wherein the final assay is performed only if the intermediate assay did not indicate the presence of a mutation, said intermediate assay providing essentially no false indications of the presence of a mutation, and fewer false indications of the absence of a mutation than the first assay.

42. A method according to claim 41, wherein the first assay is an immunoassay.

43. A method according to claim 42, wherein the intermediate assay is a nucleic acid hybridization probe-based assay.

44. A method according to claim 41, wherein the sequence of a region of a gene of interest is sequenced in course of performing the final assay.

* * * * *

SEQUENCE LISTING ( 1 ) GENERAL INFORMATION:

( i i i ) NUMBER OF SEQUENCES: 60

( 2 ) INFORMATION FOR SEQ ID NO:1:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 2 of human RB1 gene ( x i ) SEQUENCE DESCRIPTION: SEQ ID NO:1:

ACTGTGTGGT ATCCTTATTT TG                  22

( 2 ) INFORMATION FOR SEQ ID NO:2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 2 of human RB1 gene ( x i ) SEQUENCE DESCRIPTION: SEQ ID NO:2:

ATAGTGATTT GAAGTTGGTT TTA                23

( 2 ) INFORMATION FOR SEQ ID NO:3:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
    ( A ) NAME/KEY: primer for exon 3 of human RB1 gene ( x i ) SEQUENCE DESCRIPTION: SEQ ID NO:3:

ATACAGTTTT AACATAGTAT CCA                                                              23

( 2 ) INFORMATION FOR SEQ ID NO:4:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 3 of human RB1 gene ( x i ) SEQUENCE DESCRIPTION: SEQ ID NO:4:

AAGTCTATTG AGAGGAAAAT CC                                                               22

( 2 ) INFORMATION FOR SEQ ID NO:5:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 5 of human RB1 gene ( x i ) SEQUENCE DESCRIPTION: SEQ ID NO:5:

CTACTATGAC TTCTAAATTA CG                                                               22

( 2 ) INFORMATION FOR SEQ ID NO:6:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:

( A ) ORGANISM: human ( i x ) FEATURE:
    ( A ) NAME/KEY: primer for exon 5 of human RB1 gene ( x i ) SEQUENCE DESCRIPTION: SEQ ID NO:6:

TCAAGATGTT TGAGATTATT CC                                              22

( 2 ) INFORMATION FOR SEQ ID NO:7:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 13 of human RB1 gene ( x i ) SEQUENCE DESCRIPTION: SEQ ID NO:7:

TGCTTATGTT CAGTAGTTGT G                                             21

( 2 ) INFORMATION FOR SEQ ID NO:8:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 13 of human RB1 gene ( x i ) SEQUENCE DESCRIPTION: SEQ ID NO:8:

TAATGGGGTG GGAGGTAGTT T                                             21

( 2 ) INFORMATION FOR SEQ ID NO:9:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal -continued ( v i ) ORIGINAL SOURCE:
                ( A ) ORGANISM: human ( i x ) FEATURE:
                ( A ) NAME/KEY: primer for exon 25 of human RB1 gene ( x i ) SEQUENCE DESCRIPTION: SEQ ID NO:9:

TCAAACTATA ACTTGAGGTT GC        22

( 2 ) INFORMATION FOR SEQ ID NO:10:

( i ) SEQUENCE CHARACTERISTICS:
                ( A ) LENGTH: 22
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( i x ) FEATURE:
                ( A ) NAME/KEY: primer for exon 25 of human RB1 gene ( x i ) SEQUENCE DESCRIPTION: SEQ ID NO:10:

AAAGAAATTG GTATAAGCCA GG        22

( 2 ) INFORMATION FOR SEQ ID NO:11:

( i ) SEQUENCE CHARACTERISTICS:
                ( A ) LENGTH: 19
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( v i i i ) POSITION IN GENOME:
                ( A ) CHROMOSOME/SEGMENT: chromosome 15

( i x ) FEATURE:
                ( A ) NAME/KEY: primer for amplification of control region from
                        chromsome 15

( x i ) SEQUENCE DESCRIPTION: SEQ ID NO:11:

CTCACCCGCA CCTAAGTTT        19

( 2 ) INFORMATION FOR SEQ ID NO:12:

( i ) SEQUENCE CHARACTERISTICS:
                ( A ) LENGTH: 21
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no (iv) ANTI-SENSE: no (v) FRAGMENT TYPE: internal (vi) ORIGINAL SOURCE:
                (A) ORGANISM: human (viii) POSITION IN GENOME:
                (A) CHROMOSOME/SEGMENT: chromosome 15

(ix) FEATURE:
                (A) NAME/KEY: primer for amplification of control region from
                    chromsome 15

(xi) SEQUENCE DESCRIPTION: SEQ ID NO:12:

CCAGGATGAG AGCGGATGGC A 21

(2) INFORMATION FOR SEQ ID NO:13:

(i) SEQUENCE CHARACTERISTICS:
                (A) LENGTH: 19
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
                (A) ORGANISM: human (ix) FEATURE:
                (A) NAME/KEY: primer for exon 1 of human RB1 gene (xi) SEQUENCE DESCRIPTION: SEQ ID NO:13:

GCCCCAGTTC CCCACAGAC 19

(2) INFORMATION FOR SEQ ID NO:14:

(i) SEQUENCE CHARACTERISTICS:
                (A) LENGTH: 19
                (B) TYPE: nucleic acid
                (C) STRANDEDNESS: single
                (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
                (A) ORGANISM: human (ix) FEATURE:
                (A) NAME/KEY: primer for exon 1 of human RB1 gene (xi) SEQUENCE DESCRIPTION: SEQ ID NO:14:

ACCCCTCGCC CAAGAACCC 19

(2) INFORMATION FOR SEQ ID NO:15:

(i) SEQUENCE CHARACTERISTICS:
                (A) LENGTH: 21
                (B) TYPE: nucleic acid
                (C) STRANDEDNESS: single ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 8 of human RB1 gene ( x i ) SEQUENCE DESCRIPTION: SEQ ID NO:15:

TCTAATGAAA CCTAATAAGT A                    21

( 2 ) INFORMATION FOR SEQ ID NO:16:

( i ) SEQUENCE CHARACTERISTICS:
                ( A ) LENGTH: 21
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( i x ) FEATURE:
                ( A ) NAME/KEY: primer for exon 8 of human RB1 gene ( x i ) SEQUENCE DESCRIPTION: SEQ ID NO:16:

TGCTCATAAC AAAAGAAGTA A                    21

( 2 ) INFORMATION FOR SEQ ID NO:17:

( i ) SEQUENCE CHARACTERISTICS:
                ( A ) LENGTH: 21
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
                ( A ) ORGANISM: human ( i x ) FEATURE:
                ( A ) NAME/KEY: primer for exon 18 of human RB1 gene ( x i ) SEQUENCE DESCRIPTION: SEQ ID NO:17:

TTTTTGTGTG TGGGAAGTAC A                    21

( 2 ) INFORMATION FOR SEQ ID NO:18:

( i ) SEQUENCE CHARACTERISTICS:
                ( A ) LENGTH: 22
                ( B ) TYPE: nucleic acid (C) STRANDEDNESS: single
(D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
　　(A) ORGANISM: human (ix) FEATURE:
　　(A) NAME/KEY: primer for exon 18 of human RB1 gene (xi) SEQUENCE DESCRIPTION: SEQ ID NO:18:

ATTCTATTCC CTACAGTTTC TT    22

(2) INFORMATION FOR SEQ ID NO:19:

(i) SEQUENCE CHARACTERISTICS:
　　(A) LENGTH: 20
　　(B) TYPE: nucleic acid
　　(C) STRANDEDNESS: single
　　(D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
　　(A) ORGANISM: human (ix) FEATURE:
　　(A) NAME/KEY: primer for exon 21 of human RB1 gene (xi) SEQUENCE DESCRIPTION: SEQ ID NO:19:

GGCTAAAAGA AAGAAAATGG    20

(2) INFORMATION FOR SEQ ID NO:20:

(i) SEQUENCE CHARACTERISTICS:
　　(A) LENGTH: 20
　　(B) TYPE: nucleic acid
　　(C) STRANDEDNESS: single
　　(D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
　　(A) ORGANISM: human (ix) FEATURE:
　　(A) NAME/KEY: primer for exon 21 of human RB1 gene (xi) SEQUENCE DESCRIPTION: SEQ ID NO:20:

TTACCTATGT TATGTTATGG    20

(2) INFORMATION FOR SEQ ID NO:21:

(i) SEQUENCE CHARACTERISTICS:
　　(A) LENGTH: 22

( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 22 of human RB1 gene ( x i ) SEQUENCE DESCRIPTION: SEQ ID NO:21:

TATGTGCTTC TTACCAGTCA AA    22

( 2 ) INFORMATION FOR SEQ ID NO:22:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 23 of human RB1 gene ( x i ) SEQUENCE DESCRIPTION: SEQ ID NO:22:

GGAGTCATTT TTGTTGGTGT TG    22

( 2 ) INFORMATION FOR SEQ ID NO:23:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
( A ) ORGANISM: human ( i x ) FEATURE:
( A ) NAME/KEY: primer for exon 23 of human RB1 gene ( x i ) SEQUENCE DESCRIPTION: SEQ ID NO:23:

AATCTAATGT AATGGGTCCA CC    22

( 2 ) INFORMATION FOR SEQ ID NO:24:

( i ) SEQUENCE CHARACTERISTICS:

( A ) LENGTH: 22
            ( B ) TYPE: nucleic acid
            ( C ) STRANDEDNESS: single
            ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 23 of human RB1 gene ( x i ) SEQUENCE DESCRIPTION: SEQ ID NO:24:

ATCAAAATAA TCCCCCTCTC AT        22

( 2 ) INFORMATION FOR SEQ ID NO:25:

( i ) SEQUENCE CHARACTERISTICS:
            ( A ) LENGTH: 20
            ( B ) TYPE: nucleic acid
            ( C ) STRANDEDNESS: single
            ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 6 of human RB1 gene ( x i ) SEQUENCE DESCRIPTION: SEQ ID NO:25:

AAAGAAACAC CCAAAAGATA        20

( 2 ) INFORMATION FOR SEQ ID NO:26:

( i ) SEQUENCE CHARACTERISTICS:
            ( A ) LENGTH: 22
            ( B ) TYPE: nucleic acid
            ( C ) STRANDEDNESS: single
            ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
            ( A ) ORGANISM: human ( i x ) FEATURE:
            ( A ) NAME/KEY: primer for exon 6 of human RB1 gene ( x i ) SEQUENCE DESCRIPTION: SEQ ID NO:26:

TAATAAGCCA AGCAGAGAAT GA        22

( 2 ) INFORMATION FOR SEQ ID NO:27:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 7 of human RB1 gene ( x i ) SEQUENCE DESCRIPTION: SEQ ID NO:27:

TTATGGATAT ACTCTACCCT GC    22

( 2 ) INFORMATION FOR SEQ ID NO:28:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 7 of human RB1 gene ( x i ) SEQUENCE DESCRIPTION: SEQ ID NO:28:

CCTCCATTTG TTGTATTTTG AC    22

( 2 ) INFORMATION FOR SEQ ID NO:29:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 9 of human RB1 gene ( x i ) SEQUENCE DESCRIPTION: SEQ ID NO:29:

TCAAGAGTCA AGAGATTAGA    20

( 2 ) INFORMATION FOR SEQ ID NO:30:

( i ) SEQUENCE CHARACTERISTICS:
   ( A ) LENGTH: 22
   ( B ) TYPE: nucleic acid
   ( C ) STRANDEDNESS: single
   ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
   ( A ) ORGANISM: human ( i x ) FEATURE:
   ( A ) NAME/KEY: primer for exon 9 of human RB1 gene ( x i ) SEQUENCE DESCRIPTION: SEQ ID NO:30:

ATTATCCTCC CTCCACAGTC TC    22

( 2 ) INFORMATION FOR SEQ ID NO:31:

( i ) SEQUENCE CHARACTERISTICS:
      ( A ) LENGTH: 19
      ( B ) TYPE: nucleic acid
      ( C ) STRANDEDNESS: single
      ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
      ( A ) ORGANISM: human ( i x ) FEATURE:
      ( A ) NAME/KEY: primer for exon 10 of human RB1 gene ( x i ) SEQUENCE DESCRIPTION: SEQ ID NO:31:

GTGCTGAGAG ATGTAATGA    19

( 2 ) INFORMATION FOR SEQ ID NO:32:

( i ) SEQUENCE CHARACTERISTICS:
      ( A ) LENGTH: 19
      ( B ) TYPE: nucleic acid
      ( C ) STRANDEDNESS: single
      ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
      ( A ) ORGANISM: human ( i x ) FEATURE:
      ( A ) NAME/KEY: primer for exon 10 of human RB1 gene ( x i ) SEQUENCE DESCRIPTION: SEQ ID NO:32:

TATCTAAAGC AAATCAATC    19

( 2 ) INFORMATION FOR SEQ ID NO:33:

( i ) SEQUENCE CHARACTERISTICS:
    ( A ) LENGTH: 20
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 11 of human RB1 gene ( x i ) SEQUENCE DESCRIPTION: SEQ ID NO:33:

TGAGACAACA GAAGCATTAT                                             20

( 2 ) INFORMATION FOR SEQ ID NO:34:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 11 of human RB1 gene ( x i ) SEQUENCE DESCRIPTION: SEQ ID NO:34:

TGAACAAATC TGAAACACTA T                                           21

( 2 ) INFORMATION FOR SEQ ID NO:35:

( i ) SEQUENCE CHARACTERISTICS:
    ( A ) LENGTH: 22
    ( B ) TYPE: nucleic acid
    ( C ) STRANDEDNESS: single
    ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
    ( A ) ORGANISM: human ( i x ) FEATURE:
    ( A ) NAME/KEY: primer for exon 12 of human RB1 gene ( x i ) SEQUENCE DESCRIPTION: SEQ ID NO:35:

CTCCCTTCAT TGCTTAACAC AT                                          22

( 2 ) INFORMATION FOR SEQ ID NO:36:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 12 of human RB1 gene ( x i ) SEQUENCE DESCRIPTION: SEQ ID NO:36:

AAAAGCAAGA AAAGATTATG G                                21

( 2 ) INFORMATION FOR SEQ ID NO:37:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 27 of human RB1 gene ( x i ) SEQUENCE DESCRIPTION: SEQ ID NO:37:

ACTTACCCAG TACCATCAAT GC                               22

( 2 ) INFORMATION FOR SEQ ID NO:38:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 27 of human RB1 gene ( x i ) SEQUENCE DESCRIPTION: SEQ ID NO:38:

TCAAGTGGCT TAGGAATCAC CC                               22

( 2 ) INFORMATION FOR SEQ ID NO:39:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 4 of human RB1 gene ( x i ) SEQUENCE DESCRIPTION: SEQ ID NO:39:

TTGAAAACGA AATAACAC                                               18

( 2 ) INFORMATION FOR SEQ ID NO:40:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 4 of human RB1 gene ( x i ) SEQUENCE DESCRIPTION: SEQ ID NO:40:

ATAAAAAATC AGAGTGTAAC CC                                    22

( 2 ) INFORMATION FOR SEQ ID NO:41:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 14 of human RB1 gene ( x i ) SEQUENCE DESCRIPTION: SEQ ID NO:41:

GTGATTTTCT AAAATAGCAG GC                                                                    22

(2) INFORMATION FOR SEQ ID NO:42:

(i) SEQUENCE CHARACTERISTICS:
        (A) LENGTH: 19
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 14 of human RB1 gene (xi) SEQUENCE DESCRIPTION: SEQ ID NO:42:

CCAGGATGAT CTTGATGCC                                                                        19

(2) INFORMATION FOR SEQ ID NO:43:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 20 of human RB1 gene (xi) SEQUENCE DESCRIPTION: SEQ ID NO:43:

GAAAAGAGTG GTAGAAAAGA GG                                                                    22

(2) INFORMATION FOR SEQ ID NO:44:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 20 of human RB1 gene (xi) SEQUENCE DESCRIPTION: SEQ ID NO:44:

TAACAAGTAA GTAGGGAGGA GA                                             22

( 2 ) INFORMATION FOR SEQ ID NO:45:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 24 of human RB1 gene ( x i ) SEQUENCE DESCRIPTION: SEQ ID NO:45:

GTATTTATGC TCATCTCTGC                                                20

( 2 ) INFORMATION FOR SEQ ID NO: 46:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 24 of human RB1 gene ( x i ) SEQUENCE DESCRIPTION: SEQ ID NO:46:

GTGTTTGAAT AACTGCATTT GG                                             22

( 2 ) INFORMATION FOR SEQ ID NO:47:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 26 of human RB1 gene ( x i ) SEQUENCE DESCRIPTION: SEQ ID NO:47:

CGAAAGCATC ATAGTTACTG G  21

( 2 ) INFORMATION FOR SEQ ID NO:48:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 26 of human RB1 gene ( x i ) SEQUENCE DESCRIPTION: SEQ ID NO:48:

ATATAACGAA AAGACTTCTT GC  22

( 2 ) INFORMATION FOR SEQ ID NO:49:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exons 15 and 16 of human RB1 gene ( x i ) SEQUENCE DESCRIPTION: SEQ ID NO:49:

CAATGCTGAC ACAAATAAGG TT  22

( 2 ) INFORMATION FOR SEQ ID NO:50:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exons 15 and 16 of human RB1 gene ( x i ) SEQUENCE DESCRIPTION: SEQ ID NO:50:

CCCCCGACCA AAGAAACACA 20

( 2 ) INFORMATION FOR SEQ ID NO:51:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 17 of human RB1 gene ( x i ) SEQUENCE DESCRIPTION: SEQ ID NO:51:

ACCTTTCTAC TGTTTTCTTT GT 22

( 2 ) INFORMATION FOR SEQ ID NO:52:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 17 of human RB1 gene ( x i ) SEQUENCE DESCRIPTION: SEQ ID NO:52:

AAACACCTCT CACTAACAAT 20

( 2 ) INFORMATION FOR SEQ ID NO:53:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:

(A) NAME/KEY: primer for exon 19 of human RB1 gene (xi) SEQUENCE DESCRIPTION: SEQ ID NO:53:

TGTATAATCT GTGATTCTTA GC 22

(2) INFORMATION FOR SEQ ID NO:54:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 19 of human RB1 gene (xi) SEQUENCE DESCRIPTION: SEQ ID NO:54:

GCAACATTAT CATTTCCATT TT 22

(2) INFORMATION FOR SEQ ID NO:55:

(i) SEQUENCE CHARACTERISTICS:
        (A) LENGTH: 18
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for promtoer region of human RB1 gene (xi) SEQUENCE DESCRIPTION: SEQ ID NO:55:

CCCACCAGAC TCTTTGTA 18

(2) INFORMATION FOR SEQ ID NO:56:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human ( i x ) FEATURE:
    ( A ) NAME/KEY: primer for promoter region of human RB1 gene ( x i ) SEQUENCE DESCRIPTION: SEQ ID NO:56:

ACGTCCCTG AGAAAAACCG GA                                    22

( 2 ) INFORMATION FOR SEQ ID NO:57:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 4 of human RB1 gene ( x i ) SEQUENCE DESCRIPTION: SEQ ID NO:57:

ATATAGTAGT GATTTGATGT                                      20

( 2 ) INFORMATION FOR SEQ ID NO:58:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human ( i x ) FEATURE:
        ( A ) NAME/KEY: primer for exon 4 of human RB1 gene ( x i ) SEQUENCE DESCRIPTION: SEQ ID NO:58:

ATGACATAAA AAATCAGAGT                                      20

( 2 ) INFORMATION FOR SEQ ID NO:59:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: no ( i v ) ANTI-SENSE: no ( v ) FRAGMENT TYPE: internal ( v i ) ORIGINAL SOURCE:
        ( A ) ORGANISM: human (ix) FEATURE:
    (A) NAME/KEY: primer for exon 6 of human RB1 gene (xi) SEQUENCE DESCRIPTION: SEQ ID NO:59:

CACAAAAAGA AACACCCAAA AG                                                   22

(2) INFORMATION FOR SEQ ID NO:60:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: genomic DNA (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (A) NAME/KEY: primer for exon 4 of human RB1 gene (xi) SEQUENCE DESCRIPTION: SEQ ID NO:60:

TAATAAGCCA AGCAGAGAAT GA                                                   22